(12) United States Patent
Fuerst et al.

(10) Patent No.: US 11,534,246 B2
(45) Date of Patent: Dec. 27, 2022

(54) USER INPUT DEVICE FOR USE IN ROBOTIC SURGERY

(71) Applicant: Verb Surgical Inc., Mountain View, CA (US)

(72) Inventors: Bernhard Adolf Fuerst, Sunnyvale, CA (US); Pablo E. Garcia Kilroy, Menlo Park, CA (US); Berk Gonenc, Cupertino, CA (US); Jose Luis Cordoba, Malaga (ES); Joan Savall, Palo Alto, CA (US); Alexander Barthel, Sunnyvale, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 827 days.

(21) Appl. No.: 16/439,591

(22) Filed: Jun. 12, 2019

(65) Prior Publication Data

US 2019/0380791 A1     Dec. 19, 2019

Related U.S. Application Data

(60) Provisional application No. 62/685,821, filed on Jun. 15, 2018.

(51) Int. Cl.
*G06F 19/00* (2018.01)
*A61B 34/00* (2016.01)
(Continued)

(52) U.S. Cl.
CPC ............... *A61B 34/25* (2016.02); *A47C 1/00* (2013.01); *A47C 7/723* (2018.08); *A61B 34/30* (2016.02);
(Continued)

(58) Field of Classification Search
CPC .......... A61B 34/25; A61B 34/30; A61B 34/37; A61B 34/74; A61B 90/37; A61B 90/60;
(Continued)

(56) References Cited

U.S. PATENT DOCUMENTS 6,839,595 B2   1/2005   Tepper et al.
8,831,782 B2   9/2014   Itkowitz
(Continued)

FOREIGN PATENT DOCUMENTS

EP    2671686       5/2016
WO    2019220409    11/2019

OTHER PUBLICATIONS

International Search Report and Written Opinion dated Oct. 8, 2019, Application No. PCT/US2019/037226.
(Continued)

*Primary Examiner* — Abby Y Lin
*Assistant Examiner* — Sohana Tanju Khayer
(74) *Attorney, Agent, or Firm* — Womble Bond Dickinson (US) LLP

(57) ABSTRACT

User input devices (UIDs) for controlling a surgical robotic system are described. A UID can include one or more tracking sensors to generate respective spatial state signals in accordance with a pose of the UID. At least one of the tracking sensors can be a camera. In the case of multiple tracking sensors, the spatial state signals are processed by a sensor fusion algorithm to generate a more robust, single tracking signal and a quality measure. The tracking signal and the quality measure are then used by a digital control system to control motion of a surgical robotic system actuator that is associated with the UID. Other embodiments are also described and claimed.

20 Claims, 8 Drawing Sheets

(51) Int. Cl.

| | |
|---|---|
| *A61B 34/37* | (2016.01) |
| *A61B 90/00* | (2016.01) |
| *A61B 34/30* | (2016.01) |
| *A61B 90/60* | (2016.01) |
| *A47C 7/72* | (2006.01) |
| *A47C 1/00* | (2006.01) |
| *B25J 13/08* | (2006.01) |
| *B25J 13/00* | (2006.01) |
| *B25J 9/16* | (2006.01) |
| *G06F 3/0346* | (2013.01) |
| *A61B 34/20* | (2016.01) |
| *A61B 17/00* | (2006.01) |
| *G06F 3/0354* | (2013.01) |

(52) U.S. Cl.
CPC .............. *A61B 34/37* (2016.02); *A61B 34/74* (2016.02); *A61B 90/37* (2016.02); *A61B 90/60* (2016.02); *B25J 9/16* (2013.01); *B25J 13/00* (2013.01); *B25J 13/087* (2013.01); *G06F 3/0346* (2013.01); *A61B 2017/00212* (2013.01); *A61B 2034/2048* (2016.02); *A61B 2034/2051* (2016.02); *A61B 2034/2057* (2016.02); *A61B 2090/3937* (2016.02); *B25J 9/1694* (2013.01); *G06F 3/03547* (2013.01)

(58) Field of Classification Search
CPC .. A61B 2017/00212; A61B 2034/2048; A61B 2034/2051; A61B 2034/2057; A61B 2090/3937; A61B 2017/00973; A47C 1/00; A47C 7/723; B25J 9/16; B25J 13/00; B25J 13/087; B25J 9/1694; G06F 3/0346; G06F 3/03547

See application file for complete search history.

(56) References Cited

U.S. PATENT DOCUMENTS

| | | | |
|---|---|---|---|
| 10,248,652 B1* | 4/2019 | Venkataraman | ..... G06V 30/228 |
| 10,568,703 B2 | 2/2020 | Nobles et al. | |
| 2002/0188193 A1 | 12/2002 | Biglieri et al. | |
| 2003/0144590 A1 | 7/2003 | Maschke | |
| 2003/0171678 A1 | 9/2003 | Batten et al. | |
| 2004/0236541 A1 | 11/2004 | Kramer et al. | |
| 2007/0285386 A1* | 12/2007 | Lim | ..... G06F 3/0346 345/156 |
| 2011/0118748 A1 | 5/2011 | Itkowitz | |
| 2012/0071892 A1 | 3/2012 | Itkowitz et al. | |
| 2012/0316681 A1 | 12/2012 | Hagn et al. | |
| 2013/0150709 A1* | 6/2013 | Baumgartner | ..... A61B 17/8866 600/424 |
| 2014/0018960 A1 | 1/2014 | Itkowitz | |
| 2016/0270868 A1* | 9/2016 | Randle | ............. A61B 17/00234 |
| 2017/0042625 A1 | 2/2017 | Sartor | |
| 2017/0102772 A1 | 4/2017 | Hesch et al. | |
| 2017/0307891 A1* | 10/2017 | Bucknor | ................. G06F 3/012 |
| 2018/0036088 A1 | 2/2018 | Kilroy et al. | |
| 2018/0078319 A1 | 3/2018 | Nobles et al. | |
| 2018/0092706 A1 | 4/2018 | Anderson et al. | |
| 2018/0161108 A1* | 6/2018 | Savall | ..................... A61B 34/76 |
| 2018/0168759 A1* | 6/2018 | Kilroy | .................... B25J 13/025 |
| 2019/0007537 A1* | 1/2019 | Li | ....................... G06F 3/03545 |
| 2019/0282175 A1* | 9/2019 | Hill | ...................... A61B 5/7221 |

OTHER PUBLICATIONS

Goh, A.H.W., et al. "Interactive PTZ Camera Control System Using Wii Remote and Infrared Sensor Bar", World Academy of Science, Engineering, and Technology 46, 2008, pp. 127-132.

Olson, Edwin, "AprilTag: A robust and flexible visual fiducial system", IEEE International Conference on Robotics and Automation, May 9, 2011, 8 pages.

Yaniv, Ziv, et al., "Electromagnetic tracking in the clinical environment", Med. Phys. 36 (3), Mar. 2009, pp. 876-892.

International Preliminary Report on Patentability for International Application No. PCT/US2019/037226 dated Dec. 24, 2020, 9 pages.

Non-Final Office Action for U.S. Appl. No. 16/440,844 dated Jul. 9, 2021, 23 pages.

Notice of Allowance for U.S. Appl. No. 16/440,844 dated Nov. 4, 2021, 12 pages.

Extended European Search Report for European Application No. 19818641.3 dated Dec. 23, 2021, 7 pages.

* cited by examiner

USER INPUT DEVICE FOR USE IN ROBOTIC SURGERY

This non-provisional patent application claims the benefit of the earlier filing date of U.S. provisional application No. 62/685,821 filed Jun. 15, 2018.

BACKGROUND

Field

Embodiments related to robotic systems are disclosed. More particularly, embodiments related to surgical robotic systems and corresponding user input devices are disclosed.

Background Information

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon to control a robotically-assisted tool located at an operating table. The surgeon may use a computer console located in the operating room, or it may be located in a different city, to command a robot to manipulate the surgical tool mounted on the operating table. The robotically-controlled surgical tool can be a grasper mounted on a robotic arm. Accordingly, the surgical robotic system may be controlled by the remote surgeon to grasp tissue during a robotic surgery.

Control of the surgical robotic system may require control inputs from the surgeon. For example, the surgeon may hold in her hand a user input device, UID, such as a joystick or a computer mouse that she manipulates to generate the signals for the control commands that control motion of the surgical robotic system components, e.g., an actuator, a robotic arm, and/or a surgical tool of the robotic system.

SUMMARY

Existing UIDs that rely on a single tracking modality are spatially limited and prone to error. Such errors can generate undesired and potentially hazardous movement of the robotic manipulator. In the case of medical applications, movements in the sub-millimeter (for translation) and sub-degree (for orientation) range may be required to achieve clinically feasible operation. It is noted that system noise, which can lead to control errors, may be reduced by filtering the control signal from the UID. Signal filtering, however, can introduce latency that has associated undesirable effects on the stable operation of the robotic manipulator. Accordingly, a noise-free, accurate, and real-time sensing methodology is needed to detect the status, position, and orientation of the UID used for the control of surgical robotic systems.

An aspect of the disclosure here is a UID for controlling a surgical robotic system that is based on a combination of several tracking modalities (in contrast with a UID that relies on a single tracking modality which may be spatially limited and prone to error.) The tracking modalities can include a visual modality and an inertial modality to enable the estimation of a pose of the UID. A visual/inertial odometry method fuses i) an estimation of the pose based on the visual modality with ii) an estimation of the pose based on the inertial modality. More particularly, estimations of the pose computed using imaging optics are combined with measurements of a tracking sensor such as an inertial measurement unit (IMU) and/or an electromagnet (EM) sensor, to generate an accurate pose determination. The UID may enable robust and fast (e.g., real-time) tracking over a wide (unrestricted) range of motion; tracking that is immune to EM noise or distortions; and tracking that can detect and compensate for objects or people in a surrounding environment.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Embodiments of a user input device (UID) for controlling a robotic system, and more particularly a surgical robotic system are described. The UID may, however, be used to control other medical systems, such as interventional cardiology systems or medical vision systems, to name only a few possible applications.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction away from a reference point, e.g., away from an operator. Similarly, "proximal" may indicate a location in a second direction opposite to the first direction, e.g., toward the operator. Such terms are provided to establish relative frames of reference, however, and are not intended to limit the use or orientation of a UID to a specific configuration described in the various embodiments below.

Figure 1:
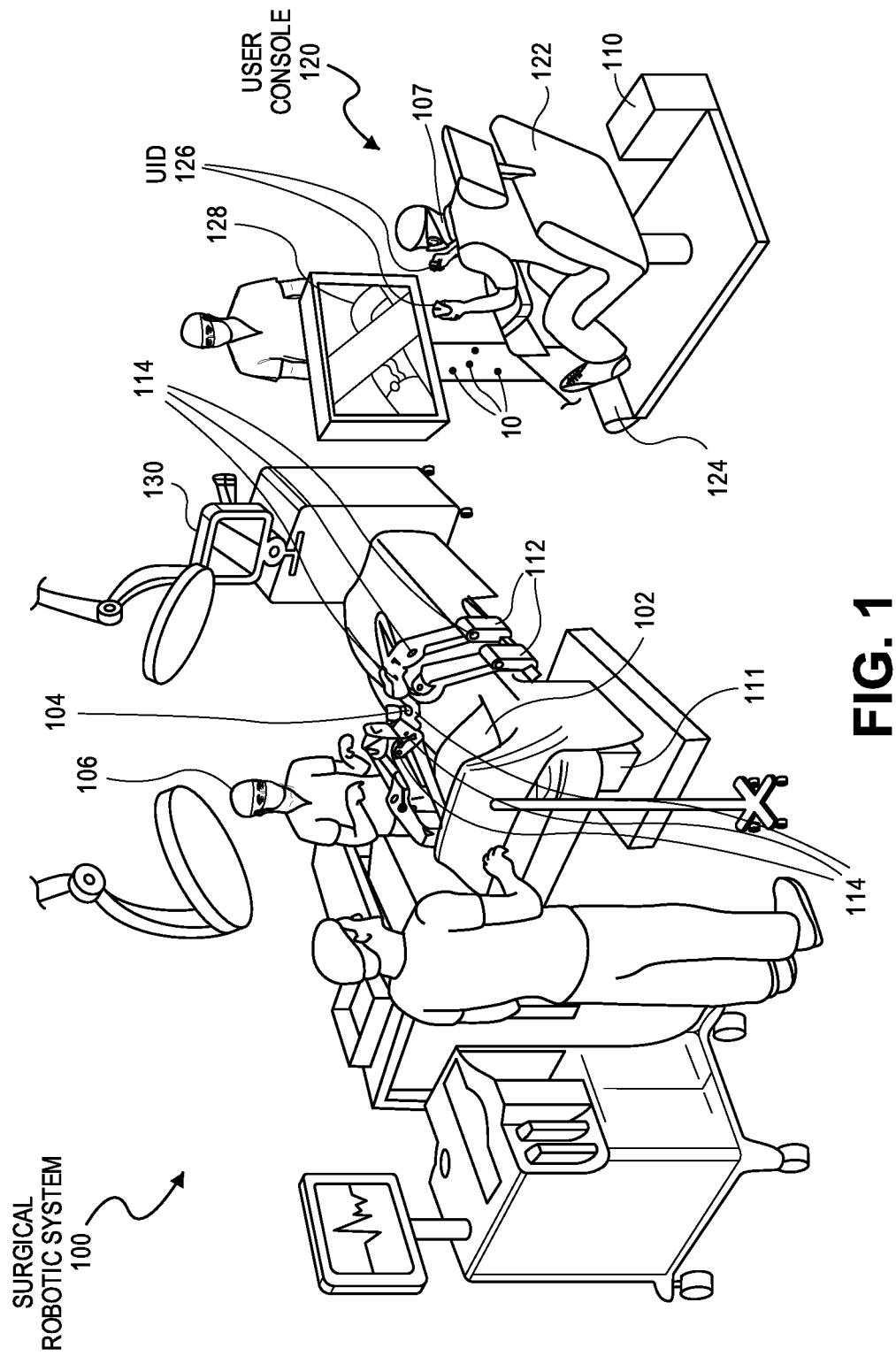
FIG. 1 is a pictorial view of an example surgical robotic system in an operating arena, in accordance with an embodiment.

FIG. 1 is a pictorial view of an example surgical robotic system 100 in an operating arena. The robotic system 100 includes a user console 120, a control tower 130, and one or more surgical robotic arms 112 at a surgical robotic platform 111, e.g., a table, a bed, etc. The system 100 can incorporate any number of devices, tools, or accessories used to perform surgery on a patient 102. For example, the system 100 may include one or more surgical tools 104 used to perform surgery. A surgical tool 104 may be an end effector that is attached to a distal end of a surgical arm 112, for executing a surgical procedure.

Each surgical tool 104 may be manipulated manually, robotically, or both, during the surgery. For example, surgical tool 104 may be a tool used to enter, view, or manipulate an internal anatomy of patient 102. In an embodiment, surgical tool 104 is a grasper that can grasp tissue of patient 102. Surgical tool 104 may be controlled manually, by a bedside operator 106; or it may be controlled robotically, via actuated movement of the surgical robotic arm 112 to which it is attached. Robotic arms 112 are shown as a table-mounted system, but in other configurations the arms 112 may be mounted in a cart, ceiling or sidewall, or in another suitable structural support.

Generally, a remote operator 107, such as a surgeon or other operator, may use the user console 120 to remotely manipulate the arms 112 and/or surgical tools 104, e.g., by teleoperation. The user console 120 may be located in the same operating room as the rest of the system 100, as shown in FIG. 1. In other environments however, the user console 120 may be located in an adjacent or nearby room, or it may be at a remote location, e.g., in a different building, city, or country. The user console 120 may comprise a seat 122, foot-operated controls 124, one or more handheld user input devices, UIDs 126, and at least one operator display 128 configured to display, for example, a view of the surgical site inside patient 102. In the example user console 120, remote operator 107 is sitting in seat 122 and viewing the operator display 128 while manipulating a foot-operated control 124 and a handheld UID 126 in order to remotely control the arms 112 and surgical tools 104 (that are mounted on the distal ends of the arms 112). Foot-operated control(s) 124 can be foot pedals, such as seven pedals, that generate motion control signals when actuated. User console 120 may include one or more additional input devices, such as a keyboard or a joystick, to receive manual inputs to control operations of user console 120 or surgical robotic system 100.

In some variations, bedside operator 106 may also operate system 100 in an "over the bed" mode, in which bedside operator 106 is now at a side of patient 102 and is simultaneously manipulating a robotically-driven tool (end effector attached to arm 112), e.g., with a handheld UID 126 held in one hand, and a manual laparoscopic tool. For example, the bedside operator's left hand may be manipulating the handheld UID 126 to control a robotic component, while the bedside operator's right hand may be manipulating a manual laparoscopic tool. Thus, in these variations, bedside operator 106 may perform both robotic-assisted minimally invasive surgery and manual laparoscopic surgery on patient 102.

During an example procedure (surgery), patient 102 is prepped and draped in a sterile fashion, and administered anesthesia. Initial access to the patient anatomy can be achieved using known techniques, such as by forming an incision in the skin. A trocar and/or other surgical tool can be inserted into the incision through the optical entry in the patient. The trocar can then be positioned at the surgical site. Initial access to the surgical site may be performed manually while the arms of the robotic system 100 are in a stowed configuration or withdrawn configuration (to facilitate access to the surgical site) or in an operator-defined parking pose. Once initial access is completed, initial positioning or preparation of the robotic system including its arms 112 may be performed. Next, the surgery proceeds with the remote operator 107 at the user console 120 utilizing the foot-operated controls 124 and the UIDs 126 to manipulate the various end effectors and perhaps an imaging system, to perform the surgery. Manual assistance may also be provided at the procedure bed or table, by sterile-gowned bedside personnel, e.g., bedside operator 106 who may perform tasks such as retracting tissues, performing manual repositioning, and tool exchange upon one or more of the robotic arms 112. Non-sterile personnel may also be present to assist remote operator 107 at the user console 120. When the procedure or surgery is completed, the system 100 and/or user console 120 may be configured or set in a state to facilitate post-operative procedures such as cleaning or sterilization and healthcare record entry or printout via user console 120.

In one embodiment, remote operator 107 holds and moves UID 126 to provide an input command to move a robot arm actuator 114 in robotic system 100. UID 126 may be communicatively coupled to the rest of robotic system 100, e.g., via a console computer system 110. UID 126 can generate spatial state signals corresponding to movement of UID 126, e.g., position and orientation of the handheld housing of the UID, and the spatial state signals may be input signals to control a motion of the robot arm actuator 114. Robotic system 100 may produce control signals as a function of the spatial state signals, to control proportional motion of actuator 114. In one embodiment, a console processor of console computer system 110 receives the spatial state signals and generates the corresponding control signals. Based on these control signals, which control how the actuator 114 is energized to move a segment or link of arm 112, the movement of a corresponding surgical tool including an end effector that is attached to the arm may mimic the movement of UID 126. Similarly, interaction between remote operator 107 and UID 126 can generate, for example, a grip control signal that causes a jaw of a grasper of the surgical tool to close and grip the tissue of patient 102.

The sensed motion of UID 126 may alternatively be provided to control other aspects of surgical robotic system 100. For example, gestures detected by a finger clutch may generate a clutch signal to pause the motion of actuator 114 and the corresponding surgical tool 104. For example, when an operator touches the finger clutch of UID 126 with a finger, the finger clutch may generate a clutch signal, and the clutch signal may be an input signal to pause the motion of actuator 114. Similarly, one or more capacitive sensing pads may be located on UID 126, and the operator may touch the capacitive sensing pads to control a camera view of an endoscope, a cursor on a display of user console 120, etc., while performing a diagnostic, surgical, laparoscopic, or minimally invasive surgical procedure, or another robotic procedure.

Surgical robotic system 100 may include several UIDs 126 where respective control signals are generated for each UID that control the actuators and the surgical tool (end effector) of a respective arm 112. For example, remote operator 107 may move a first UID 126 to control the motion of actuator 114 that is in a left robotic arm, where the actuator responds by moving linkages, gears, etc., in that arm 112. Similarly, movement of a second UID 126 by remote operator 107 controls the motion of another actuator 114, which in turn moves other linkages, gears, etc., of the robotic system 100. Robotic system 100 may include a right arm 112 that is secured to the bed or table to the right side of the patient, and a left arm 112 that is at the left side of the patient. An actuator 114 may include one or more motors that are controlled so that they drive the rotation of a joint of arm 112, to for example change, relative to the patient, an orientation of an endoscope or a grasper of the surgical tool that is attached to that arm. Motion of several actuators 114 in the same arm 112 can be controlled by the spatial state signals generated from a particular UID 126. UIDs 126 can also control motion of respective surgical tool graspers. For example, each UID 126 can generate a respective grip signal to control motion of an actuator, e.g., a linear actuator that opens or closes jaws of the grasper at a distal end of the surgical tool to grip tissue within patient 102.

In some aspects, the communication between platform 111 and user console 120 may be through a control tower 130, which may translate operator commands that are received from user console 120 (and more particularly from console computer system 110) into robotic control commands that are transmitted to arms 112 on robotic platform 111. The control tower 130 may also transmit status and feedback from platform 111 back to user console 120. The communication connections between the robotic platform 111, user console 120, and control tower 130 may be via wired and/or wireless links, using any suitable ones of a variety of data communication protocols. Any wired connections may be optionally built into the floor and/or walls or ceiling of the operating room. Robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

It will be appreciated that the operating room scene in FIG. 1 is illustrative and may not accurately represent certain medical practices.

UID Having a Camera for Visual/Inertial Odometry

UIDs are used in the control of robotic systems, for teleoperation purposes, to provide accurate sensing of operator intent and to initiate a stable and robust motion of a robotic manipulator. Existing UIDs for controlling surgical robotic systems are based on one of several tracking modalities. These modalities include: mechanical tracking systems that sense movement of linkages of the UID and that output control signals to an actuator based on the movement, electromagnetic (EM) tracking systems that sense movement of the UID within an EM space and output control signals to an actuator based on the movement, and optical tracking systems that include a camera located external to the UID to view movement of markers on the UID (and output control signals to an actuator based on the movement.) Each of these modalities are associated with drawbacks, such as limitations placed on the free motion of the operator (holding the UID) by mechanical linkages, errors in control signals caused by inherent system noise or drift, ferromagnetic interference or distortion of EM fields caused by nearby objects, e.g., cell phones, or errors in control signals caused by nearby objects occluding a view of the UID markers by the external camera.

In one aspect, a UID for controlling a surgical robotic system is based on a combination of several tracking modalities (in contrast with a UID that relies on a single tracking modality which may be spatially limited and prone to error.) The tracking modalities can include a visual modality ("seeing" by way of digital image capture through imaging optics) and an inertial modality to enable the estimation of a pose of the UID. A visual/inertial odometry method fuses i) an estimation of the pose based on the visual modality with ii) an estimation of the pose based on the inertial modality. More particularly, visual modality refers to estimations of the pose that have been computed by analyzing digital images produced by an "outward looking" camera, i.e., whose imaging optics face forward at the distal end of the UID 26 to view a marker. The imaging optics and image sensor may be configured such that the digital images capture the scene before camera in the infrared spectrum, i.e., not necessarily in the human visible light spectrum). These are effectively combined with measurements of a tracking sensor, e.g., an inertial measurement unit (IMU) and/or an EM sensor, to generate a single tracking signal as an accurate pose determination. As described below, the UID provides: robust and fast (e.g., real-time) tracking over a wide (unrestricted) range of motion; tracking that is immune to EM noise or distortions; and tracking that can detect and compensate for objects or people in a surrounding environment.

Figure 2:
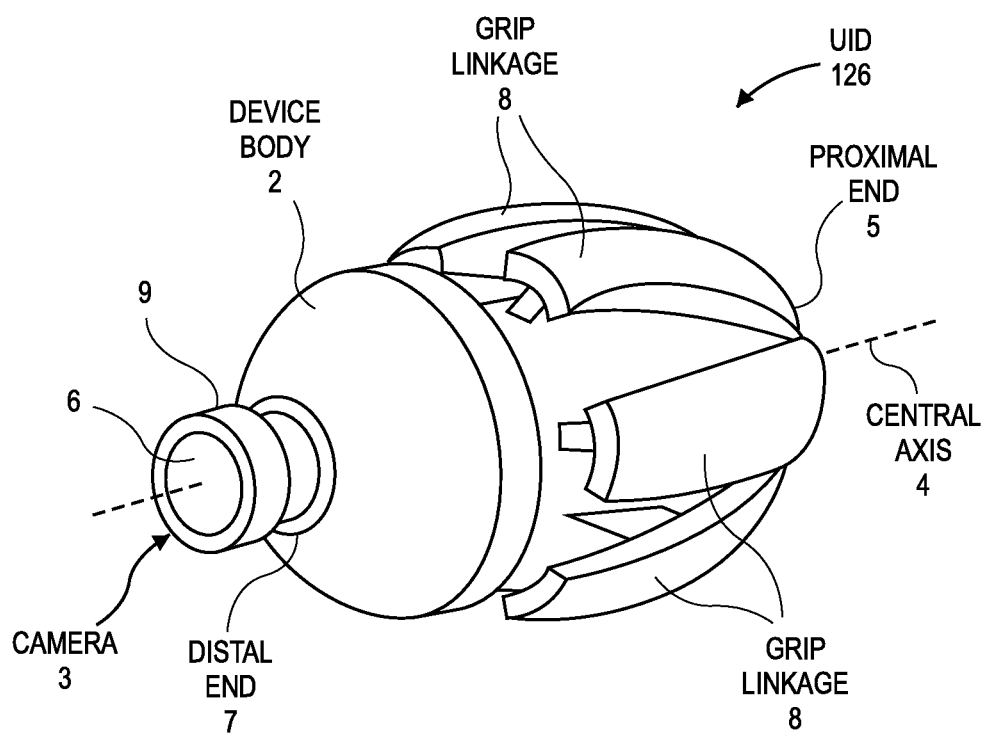
FIG. 2 is a perspective view of a user input device having a camera that is looking outward, in accordance with an embodiment.

Referring to FIG. 2, a perspective view of a UID 126 having a camera 3 with a lens 6 as imaging optics is shown in accordance with an embodiment. As described further below, the UID 126 has components for visual/inertial odometry that allow its operator to interact more reliably with a surgical robotic system than a conventional UID. The UID can control robotic instruments, other robotic components, or a graphical user interface (GUI) on a display of the surgical robotic system. In an embodiment, the UID includes a device body 2 that extends in a longitudinal direction along a central axis 4. For example, the device body may extend longitudinally from a proximal end 5, which is normally cupped within a hand of an operator, e.g., the remote operator 107, when the operator is holding the UID, to a distal end 7 having a forward-facing surface.

The UID 126 can include a gripping structure to be held by the operator. For example, the UID may include several grip linkages 8 extending outward from the centrally located device body 2. The operator may hold portions of the grip linkages between several fingers while being able to freely move the UID 126 as a whole within a workspace. The workspace may be a range of arms reach of the operator. The UID may be unrestricted by mechanical linkages that constrain a size of the workspace (also referred to here as an ungrounded UID).

In an embodiment, the grip linkages are mounted on the device body around the central axis 4. For example, the grip linkages may be distributed symmetrically about the central axis 4. Each grip linkage can include a grip crank that is pivotally coupled to the device body. For example, the grip crank may be hinged to the device body at a proximal end, and extends distally from the proximal end to a distal tip of the grip linkage. Accordingly, each grip crank may be cantilevered from the device body. The operator can squeeze the cantilevered cranks to pivot the cranks toward the device body which in response causes a sensor circuit within the device body 2 to generate a signal indicative of the angle of the squeezed crank, to control an end effector on the associated robotic arm, e.g., to generate a pinching motion by the end effector.

In an embodiment, the UID 126 also has a visual tracking modality based on data generated by a camera. The camera may be mounted on the device body 2 or integrated in a housing of the device body 2. For example, the camera can be mounted inside a housing of the device body 2, along the central axis 4 at the distal end 7 of the device body as shown, or in any position that enables it to view in a direction of the central axis 4 away from the grip linkages (e.g., the field of view of the camera is directed forward, from the forward-facing surface of the distal end 7 as for example shown in FIG. 2. The camera can include several subcomponents, including a lens (as part of imaging optics) and an associated imaging sensor that may be part of a camera module (not shown in detail). The UID can also include supporting structures, such as a lens support 9 mounted on the device body, which holds the lens, e.g., as part of the camera module. The central axis 4 of the UID may intersect the lens, e.g., coinciding with the central imaging axis of the camera. The lens may be offset from central axis 4 and may be tilted to capture images that are off axis relative to the central axis.

The camera provides visual data that is interpreted by a digital processor to determine a pose of the UID. By way of definition, the pose of the UID is a position and an orientation of the UID in the workspace. For example, the position can include 3 degrees of freedom along orthogonal axes, and the orientation can include 3 degrees of freedom about the axes. More particularly, the pose of the UID has a total of 6 degrees of freedom.

The camera can generate information about the pose of the UID by viewing an optical marker that is positioned at a known or determinable position within the workspace or the surrounding environment (outside the UID.) For example, the operator can hold the UID while sitting in the seat 122 of the user console and viewing a real-time scene of a surgical operation on the operator display 128. The camera can be pointed toward the display as the operator manipulates the UID to simulate and control movement of the surgical tool that is positioned at the displayed surgical site. In an embodiment, the marker, such as a collection of bright dots, is located around the display such that the marker is viewed by the camera. The marker can be reliably detected based on its predetermined or known size and shape, e.g., a stored data structure that describes an absolute position of the marker and for example the relative location of each of a number of objects that constitute the marker, which remains fixed during teleoperation. Given that an absolute position of the marker and its size and shape are known, e.g., at a predefined location on the user console, the pose of the camera may be accurately determined by detecting and interpreting (using pattern recognition or machine learning algorithms) objects in the digital images produced by the camera as being the marker. For example, by detecting a marker and then determining movement of the marker (e.g., changes in its shape as captured from different camera positions or angles, or changes in its position relative to the camera) in consecutive images captured by an image sensor of the camera, a movement and/or position of the camera (and hence the pose of the UID) can be accurately determined.

In addition to tracking a static marker (a marker that is stationary relative to the UID), the UID may be able to track one or more moving markers around the workspace and the surrounding environment. In an embodiment, the operator can hold two UIDs (one in each hand) to control several tools of the surgical robotic system. A first camera on a first UID may view a marker that is on a second UID. More particularly, the first UID can have a camera to track a relative position between the first UID and the second UID, and the camera (as well as tracking sensors) can also track a relative position of the first UID relative to a static marker on the user console. By determining the position of the first UID relative to both the static marker of the user console and the dynamic marker of the second UID (the UID marker is dynamic when the UIDs are being moved relative to each other), a position of the second UID relative to the static marker of the user console can be determined by association. In other words, the UIDs can be referenced to each other along with the reference of one of the UIDs to an external datum, to determine relative movement of the UIDs and movement of the UIDs within a frame of reference.

In an embodiment, only one of the two UIDs (that are to be held in the hands of the remote operator 107) has a camera. Alternatively, both UIDs have cameras that can detect markers on the other UID and/or the user console. The position detection that is based on visual data provided by the camera can be supplemented by a position determination that is based on sensor data provided by a tracking sensor, e.g., an inertial measurement unit, IMU, or an EM sensor of one of the UIDs. For example, by processing image data from the camera and sensor data from an IMU tracker or an EM tracker, a more reliable estimate of the position and orientation of both UIDs within the frame of reference can be determined.

With respect to the visual modality estimation (camera based position and/or orientation detection techniques), these may use one or more of the following features. In one instance, a marker 10 is on the user console 120 (e.g., see FIG. 1 and FIG. 3A and FIG. 3B, where in FIG. 3A the marker 10 is a collection of eight light sources that are located on a generally inverted-Y shaped stand of the operator display 128.) The marker 10 can be emitting light at a specific wavelength band (marker wavelength), for instance centered at 850 or centered at 940 nm (infrared). The camera can be configured with a band-pass filter to only observe that marker wavelength. The camera can be configured to see (image) both in the visible range and in for example the infrared range (e.g., the marker wavelength), which allows natural features to be imaged and tracked as well as marker tracking. Alternatively, an infrared pass filter that also blocks the visible spectrum may be added to the imaging path in front of the image sensor, to result in the image sensor producing images that have an essentially black background and on which the constituent light emitting structures of the marker 10 have been captured with high contrast. This solution is also independent of the visible light conditions and any changes in the visible lighting at the user console 120.

Figure 3A:
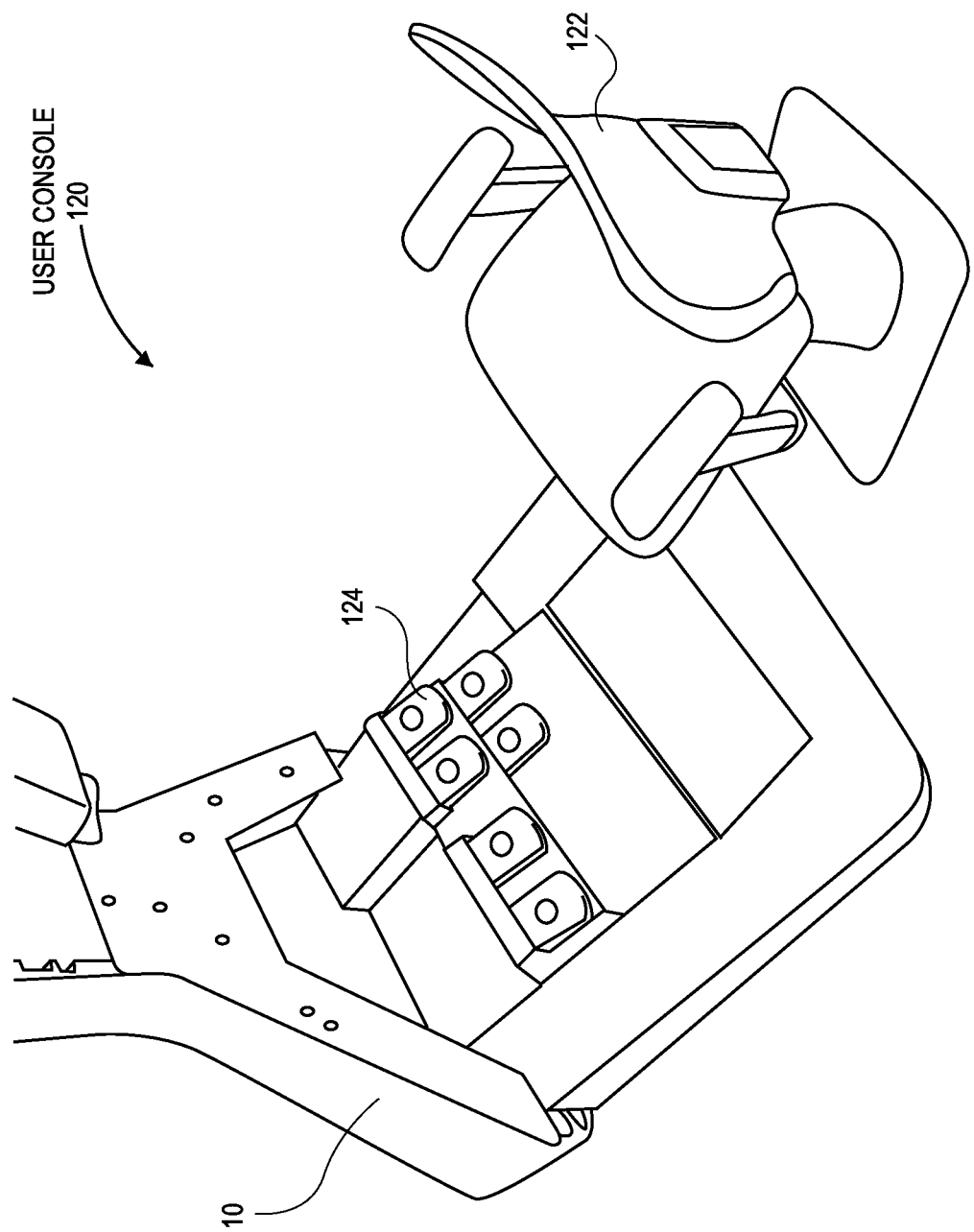
FIG. 3A shows an example arrangement for a marker used for visual or camera based tracking.
Figure 3B:
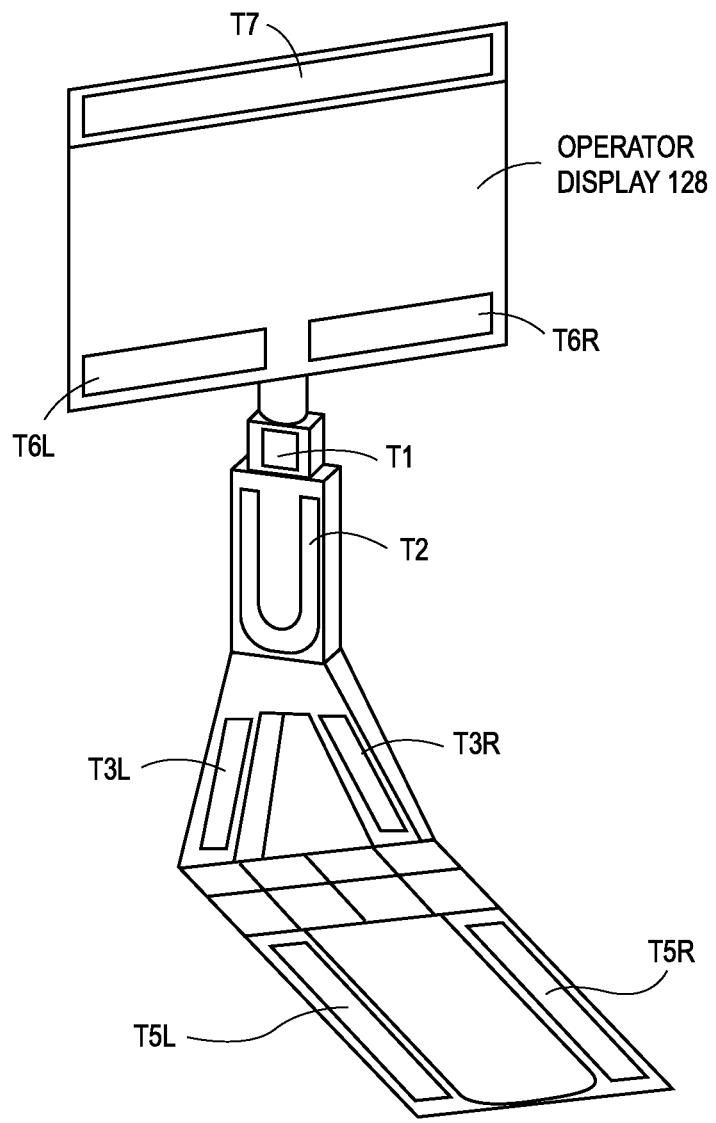
FIG. 3B shows several other arrangements for the marker at the user console.

The marker can be comprised of multiple light emitting structures, such as lines, two dimensional areas, or dots. The marker can have redundant features (e.g. more dots than needed) to allow the tracking system to tolerate partial occlusions of the marker. The layout of the marker can be a predefined shape that is based on a pseudo-random distribution of features. FIG. 3A shows an example of an inverse Y-shaped structure (e.g., a stand or support for the operator display 128) located between the foot operated controls 124 (e.g., foot pedals.) In that example, eight dots are shown that are arranged in a Y-pattern, where each dot emits light from the front face of the generally Y-shaped structure towards the seat 122 where the remote operator 107 sits—see also FIG. 1. Another example of the marker 10 is depicted in FIG. 3B, which includes a composition of light emitting segments at distinct locations: T7 above the operator display 128; T6 below the operator display 128 with a left segment T6L and a spaced apart right segment T6R; on the inverted-Y shaped stand with center segments T1 and T2 on the vertical, and a left segment T3L and a right segment T3R on the respective legs of the inverted-Y; and on the floor of the user console 120 as a left segment T5L and a spaced apart right segment T5R. Note that the marker 10 need not have all of these segments in its composition; one or more of the segments shown could be omitted yet the composition as a whole may still function as a reliable marker that has enough redundancy to tolerate partial occlusions (of some segments.) In addition, there may also be left and right marker segments on the shoulders of the operator and on a ceiling segment above the operator 107 (both not shown). A light emitting structure (as part of a self-emitting marker) may be a light emitting diode, LED, that is positioned behind material transparent to the specific marker light emission wavelength, e.g., infrared. In one embodiment, the LEDs are behind a continuous sheet of material transparent to infrared light.

Referring now to the camera 3, in one embodiment the lens 6 is a wide-angle lens, for example having a field of view of at least 90 degrees. The field of view can affect tracking efficacy of the UID. For example, a smaller field of view can decrease tracking quality, and a larger field of view can limit an angular resolution of the camera and decrease tracking accuracy at greater distances. Accordingly, the field of view may be in a range of 110-180 degrees, e.g., 170 degrees.

Figure 4:
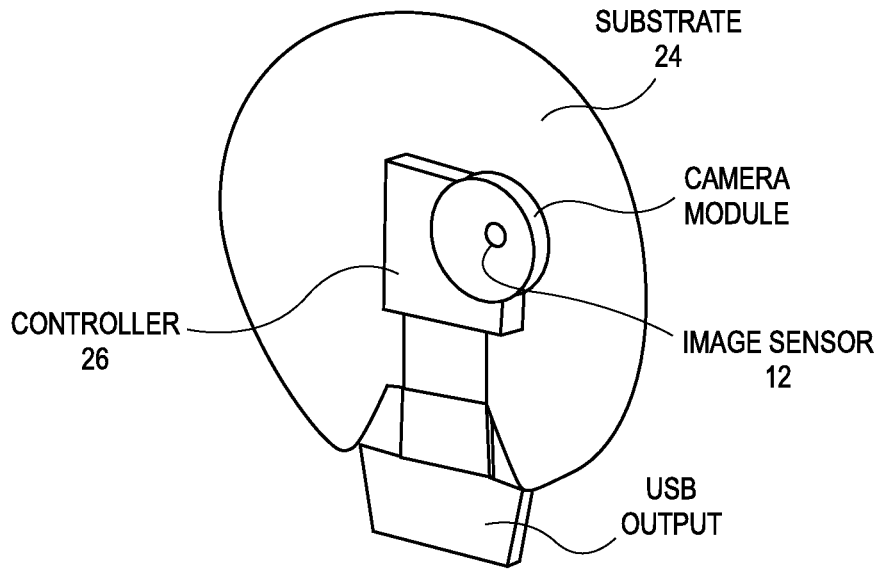
FIG. 4 is a perspective view of a printed circuit board for use in a user input device having a camera, in accordance with an embodiment.

The lens 6 can direct visible and non-visible light from a scene (e.g., that includes visible and/or non-visible light emitted by the marker 10) to an image sensor 12 of the camera module—see FIG. 4. In an embodiment, the image sensor is a CMOS image sensor having approximately 8.08 M effective pixels. More generally however, the image data captured by the image sensor can be full high definition, HD, but it could also be in a lower resolution or a higher resolution. As one example, a resolution of the camera can be 1080p (1920×1080 pixels) to achieve an RMS error in determining and tracking the position of the UID of 0.5 mm and 0.05 degrees at a distance of 60 cm from the nearest object.

In addition to lens and camera module capabilities, additional settings that can affect tracking accuracy include latency, update rate, and shutter settings of the camera. In an embodiment, accurate tracking is based on the latency between a motion of an event occurs, e.g., an operator moves the UID within the workspace, to the application or publication of the tracked pose, e.g., when the tool that is attached to the robotic arm moves in the same direction as the UID. For example, the camera module may capture images at a rate of 120 frames per second to meet and exceed the target latency. In an embodiment, the camera module includes a shutter that does not introduce motion artifacts. It has been determined that motion artifacts may be introduced by a rolling shutter. Accordingly, the camera may have a fast (adjustable) or global shutter to avoid motion artifacts.

Figure 5:
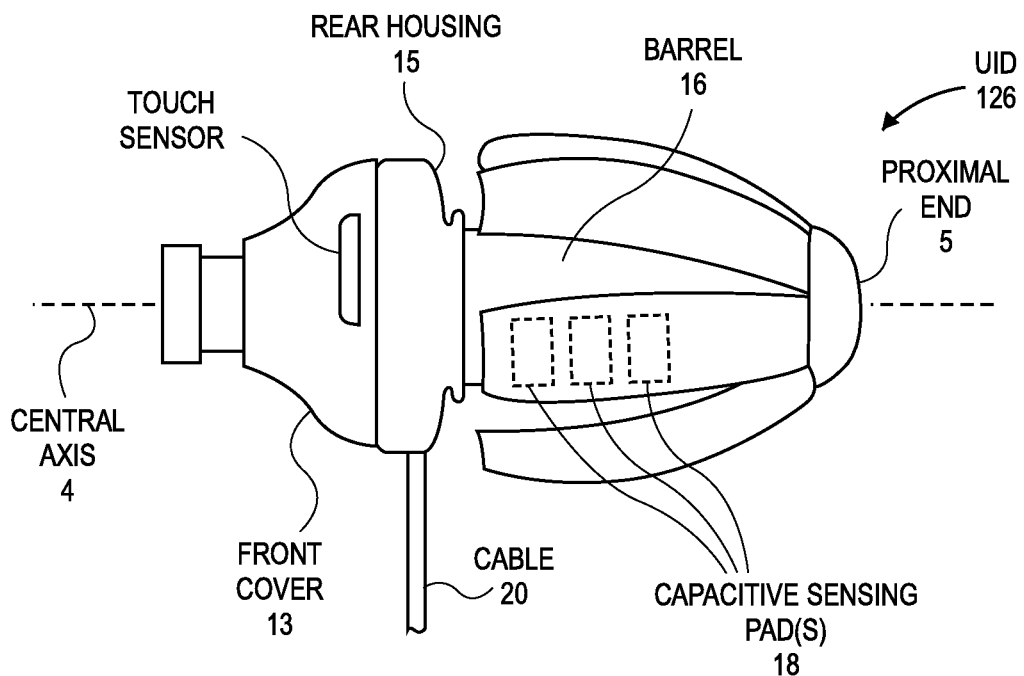
FIG. 5 is a side view of a user input device having a camera, in accordance with an embodiment.

Referring to FIG. 5, a side view of a UID 126 having a camera is shown in accordance with an embodiment in which there one or more additional sensors are in the device body 2, such as a touch sensor for detecting touch inputs, e.g., a clutch input that signals the system to clutch or pause teleoperation. The additional sensors can be located on an external surface of the device body, or may be contained within the device body. For example, the device body can include a front cover 13 that is attached to a rear housing 15. The space between the front cover and the rear housing can contain components, such as the camera module of FIG. 4 and additional tracking components. The tracking components can also be contained within a barrel 16 that extends rearward from the rear housing to the proximal end 5.

The UID 126 may include at least one capacitive sensing pad 18 on an exterior surface of each grip linkage 8 as shown. At least one grip linkage may have several capacitive sensing pads on its exterior surface, exposed to finger touch of the user. For example, the grip linkage may include a first capacitive sensing pad, a second capacitive sensing pad, and/or a third capacitive sensing pad mounted or arranged sequentially on the exterior surface of the grip linkage. For example, the first capacitive sensing pad may be distal to the second capacitive sensing pad on the exterior surface, and the second capacitive sensing pad may be distal to the third capacitive sensing pad, as shown in FIG. 5.

In an embodiment, the output signals of a linear array of grip linkage capacitive sensing pads may be monitored by a processor of the UID 126 to detect a swipe gesture by its operator. The operator may input the swipe gesture by swiping their finger over the exterior surface of the grip linkage. The swipe can cause a sequence in changes in respective capacitances of the first capacitive sensing pad, the second capacitive sensing pad, and/or the third capacitive sensing pad. The UID processor can detect the sequence of changes as a swipe gesture over the array of pads. The swipe gesture may be used to command various outputs. For example, the swipe gesture can trigger a control signal to cause the associated robotic arm to perform a predetermined operation. Alternatively, the swipe gesture can command some elements of a graphical user interface (GUI) of the user console. For example, the operator may swipe the exterior surface of the grip linkage as a control input to navigate menus, scroll a displayed view, zoom in and out from a displayed image, or control other aspects of the GUI.

In an embodiment, one or more tracking sensors are mounted within the device body 2 of the UID 126, e.g., within a volume defined inside of the front cover 13, or inside of the rear housing 15, or inside the barrel 16. The tracking sensor(s) is configured to generate a spatial state signal. A spatial state signal may be measured or sensed data relating to any aspect of the spatial state of the UID, including sensed data that varies in real-time in accordance with the pose of the UID, e.g., in response to movement of the device body 2 or in response to a given position or orientation of the device body 2 within a UID workspace at the user console 120. For example, the one or more tracking sensors can include an IMU sensor or an EM sensor. The IMU sensor and/or the EM sensor can each be capable of measuring the pose of the UID in one or more degrees of freedom.

In an embodiment, the surgical robotic system has an inertial tracking modality for the UID, where a processor interprets one or more spatial state signals being sensor data generated by the IMU to track an aspect of the position and/or orientation of the UID. The IMU can measure UID acceleration. The IMU can measure the acceleration with at least 3 degrees of freedom. For example, the IMU of the UID can include one or more accelerometers and one or more gyroscopes. The accelerometers can measure inertial acceleration of the UID along one or more axes which may be interpreted by a processor to determine changes in position of the UID, e.g., translation along an X, Y or Z axis. The gyroscopes can measure angular acceleration or turning about the one or more axes, e.g., yaw, pitch, and roll, of the UID. More generally, the IMU provides various spatial state signals (sensor data), such as accelerometer and/or gyroscope measurements, that describe the relative pose of the UID in one or more degrees of freedom.

In an embodiment, the surgical robotic system has an EM tracking modality where a processor interprets data generated by an EM sensor that is in the device body 2, to track both the position and orientation of the UID. The EM sensor can be part of an EM tracking system which also includes an EM field generator (not shown) that is positioned near the UID workspace, for example on the user console 120. The EM field generator includes one or more EM transmitters that generate an electromagnetic field within which the UID 126 is held and manipulated by the remote operator 107 (while the latter is sitting on the seat 122.) When the UID moves, an interaction between the EM sensor and the electromagnetic field occurs. This interaction is measured or sensed, for example as an electrical signal from the sensor located in the UID. The measured signal is then interpreted to describe the pose of the UID with 6 degrees of freedom. The EM tracking system determines the pose of the UID with 6 degrees of freedom, for instance 3 degrees of freedom describing the translation along axes, and 3 degrees of freedom for rotation around axes.

The UID 126 can transmit data from its camera, IMU, or EM sensor via one or more wired or wireless data connections. In an embodiment, the transmission is via a wired data connection, e.g., a cable 20 that is communicatively connected to one or more processors of the UID. The cable 20 of the UID can be routed out of the proximal end (see FIG. 6), the distal end, or a side of the device body 2. For example, the cable may exit laterally from the rear housing 15 as seen in FIG. 5, or from the volume between the front cover and the rear housing, or it may exit outward from the proximal end 5 along the central axis (FIG. 6).

In an embodiment, the cable communicates data from one or more of the UID sensors. In the case of 1080p resolution, data throughput of the camera module can be up to 2 Gbit/s (1920×1080 pixel×8 bit gray×120 frame/s=1.99 Gbit/s). The cable can be a USB cable to transmit the visual data generated by the camera module. The maximum signaling rate of USB 2.0 version, however, is defined as 480 Mbit/s. Accordingly, the cable can be a USB cable that is USB 3.0 version or higher (USB 3.0 is defined as 5 Gbit/s and USB 3.1 is defined as 10 Gbit/s).

Figure 6:
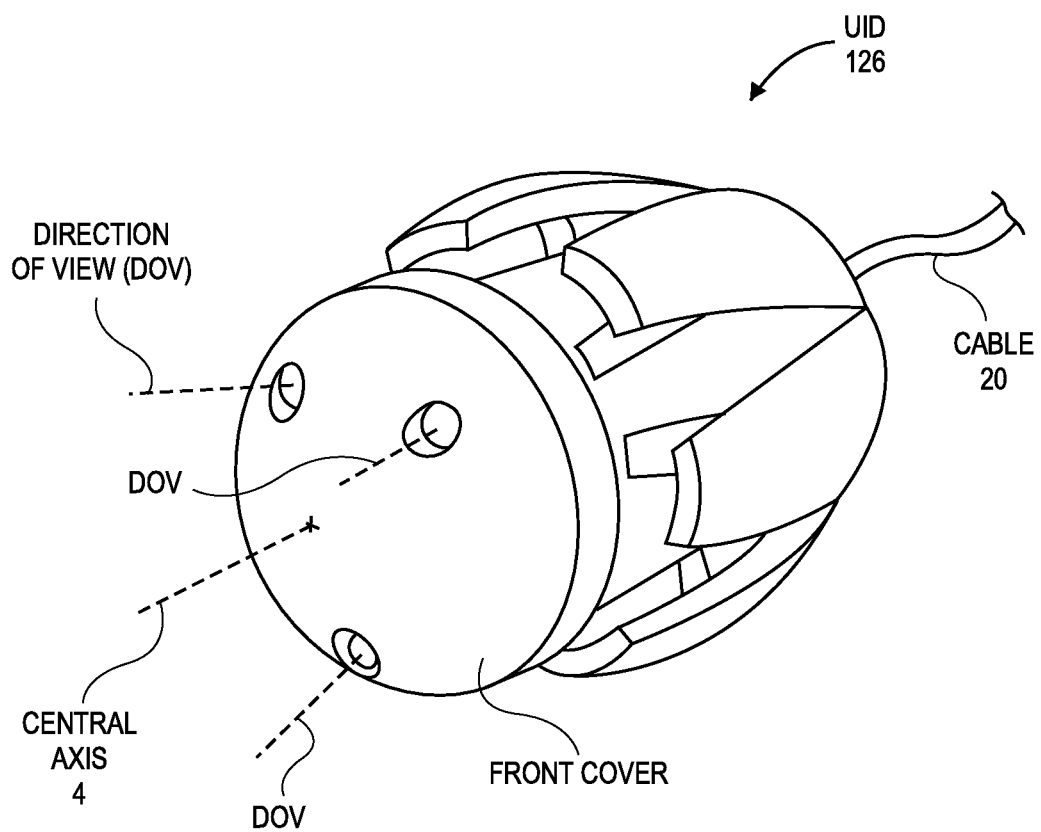
FIG. 6 is a perspective view of a user input device having several cameras, in accordance with an embodiment.

Referring to FIG. 6, a perspective view of another example of the UID 126 is shown, where the UID 126 in this case has several cameras each having a respective imaging lens (in this example, three as shown.) The lenses can be mounted on the front cover 13 of the UID and are tilted relative to each other so that their cameras have three directions of views, DOVs, relative to the central axis 4. For example, the cameras may be distributed symmetrically around the central axis and pointed in a direction that is at a non-zero angle to the central axis. Each lens may be a wide-angle lens, e.g., a lens having a field of view of at least 90°. In combination the lenses may have a combined field of view of 360° or more.

The combined field of view of several cameras can provide a field of view that allows the UID to detect a marker over a wider range of UID orientations within the workspace (as compared to a single camera.) This means the system can maintain tracking of the marker even while the operator has moved the UID to a position or pose in which the front of the UID is not facing the operator display 128, e.g., when the UID is being used in a persistently misaligned manner. Furthermore, if the cable 20 extends from the front end of the UID (not shown) and is hanging in front of one of the cameras, the portion of the image data that contains the cable can be omitted from processing (for pose estimation), to avoid image artifacts. That is because image data from another camera module can be used to compensate for the omitted imagery. Similar compensation can be performed when the operator accidentally occludes one of the cameras, e.g., moves their finger in front of that camera's lens. Since a finger of the operator is unlikely to be large enough to entirely block the field of view of every camera simultaneously, one or more of the markers in the workspace of the remote operator 107 may remain visible at all times, to one or more of the cameras. Accordingly, the redundancy of images from the several cameras ensures that one or more of the markers can be detected for accurate determination of the UID pose.

As an alternative to having a multitude of cameras for extended field of view, a single camera may be used in combination with an actuated and encoded tilting mechanism. The tilting mechanism can be controlled by the processor to automatically adjust the orientation of the camera (relative to a stationary "base" of the UID 126, e.g., a predetermined and fixed plane through the UID 126) such that the tracked marker is at all times maintained within the field of view of the camera. In this embodiment, in order to locate the UID in space (estimate its pose), a marker pose that is detected in the camera frame (the digital images produced by the camera) needs to be multiplied by the transformation between the camera frame and the UID base (which transformation may be defined by position encoder output of tilting mechanism).

Referring to FIG. 4, a perspective view of a printed circuit board (PCB) for use in the UID 126 is shown in accordance with an embodiment. Mounted to the PCB are sensors and electronic signal processing units that prepare the sensor signals for communication to an external processor (e.g., part of the console computer 110). In an embodiment, the PCB includes a substrate 24 on which the electronic components are mounted. The substrate 24 may be shaped to mount within the volume between the front cover 13 and the rear housing 15 (e.g., see FIG. 5.) One or more of the camera module, the lens, the IMU, or a microprocessor may be mounted on the substrate. Other components, such as the EM sensor, can be mounted elsewhere within the device body 2 and wired to the components mounted on the substrate.

In an embodiment, the one or more processors mounted on the substrate 24 include a UID controller 26. The controller 26 may be communicatively coupled to the image sensor 12 and the IMU (not shown.) For example, the controller can have a digital camera communications interface and general-purpose input-output pins to connect the controller to the image sensor and the sensors of the IMU. Accordingly, visual data generated by the image sensor and inertial data generated by the IMU can be simultaneously acquired by the controller 26.

The controller 26 can include data output connections to interface with other electronic components of the surgical robotic system. For example, the controller can output a data stream containing data from one or more of the camera, the IMU, or the EM sensor, to an output connection. In an embodiment, the output connection is a Universal Serial Bus, USB, output configured to connect to the cable 20. Accordingly, the controller 26 can push data via a USB 3.0 connection, for example, to another processor of the surgical robotic system, such as a processor of the console computer 110.

Figure 7:
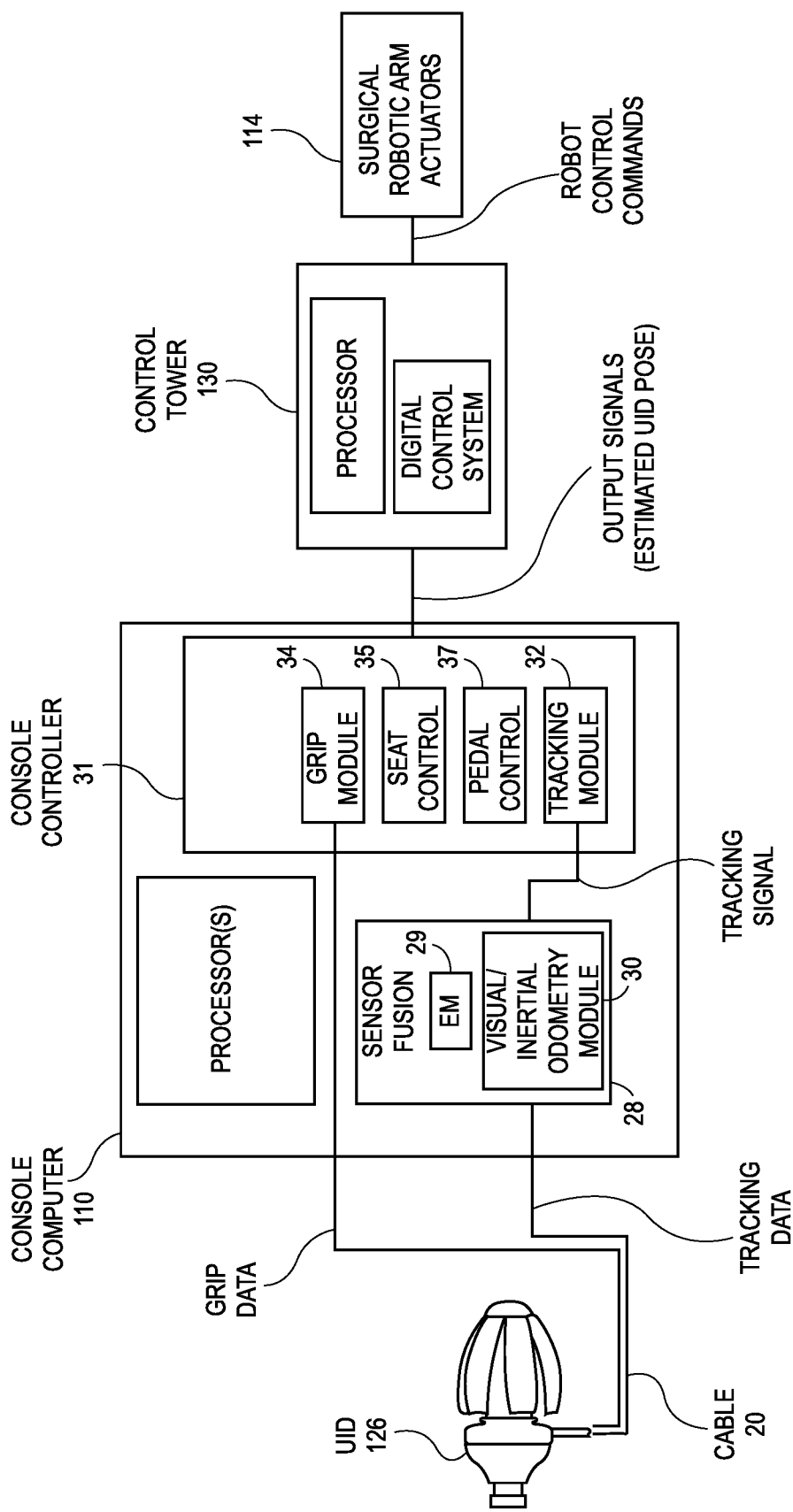
FIG. 7 is a block diagram of a surgical robotic system, in accordance with an embodiment.

Referring to FIG. 7, a block diagram of a surgical robotic system is shown in accordance with an embodiment. The cable 20 transmits image data and metadata, e.g., position or orientation data from the IMIU and/or EM tracking sensor (s), from the UID 126 to the console computer 110. In an embodiment, the cable 20 includes several wired connections running in parallel. For example, a tracking data wire that carries raw image data from the camera and raw sensor data from the tracking sensors of the UID 126 can run in parallel to a grip data wire that carries raw grip data (e.g., data from capacitive sensors or touch sensors or a mechanical switch sensor) indicative of a grip state or clutch state of the UID. The grip state may be defined by a sensed position of the grip linkages (e.g., when the operator squeezes or relaxes the grip linkages), touch inputs detected by capacitive sensors on the UID, or any other sensor data that is associated with non-tracking inputs made by the operator. In some cases, the UID controller 26 may filter the raw image data, the raw tracking sensor data, and/or the raw grip data, before sending over the cable 20.

The tracking data wire can carry the tracking data to a sensor fusion module 28 which is being executed by the processor of the console computer 110. The tracking data can include EM tracking data from EM sensor(s), image data from camera(s), and/or IMU data from IMU sensor(s). In an embodiment, the EM tracking data is input to an EM tracking system 29 of the sensor fusion module, and the image data and IMU data are input to a visual-inertial odometry module 30 of the sensor fusion module 28. The tracking data can include the image data having for example 120 frames/s at 1080p grayscale, and the IMU data sampled at 400 Hz. Existing UIDs typically include a single cable to transmit tracking data to the robotic system, and data is aggregated, collected, processed, integrated, sent, and de-serialized sequentially. Image data, however can consume a large amount of bandwidth, and thus, sequential transmission of image data and IMU data may be impractical. Accordingly, the image data and the IMU data may be simultaneously acquired, integrated, and timestamped by the UID controller 26 (see FIG. 4.) The timestamped data containing both image data and IMU data can then be sent to the visual/inertial odometry module 30. The sensor fusion module 28, which includes the visual/inertial odometry module 30, can then output a tracking signal, which is a signal defining the UID pose, to a console controller 31 (software being executed by one or more processors of the console computer 110.) The tracking signal can be stored and processed by a tracking module 32 of the console controller 31.

Fusing of the sensor data (which produces the tracking signal) from multiple sensors can enable a more precise estimation of the UID pose (position and orientation). Additional details of the sensor fusion are described below.

Figure 8:
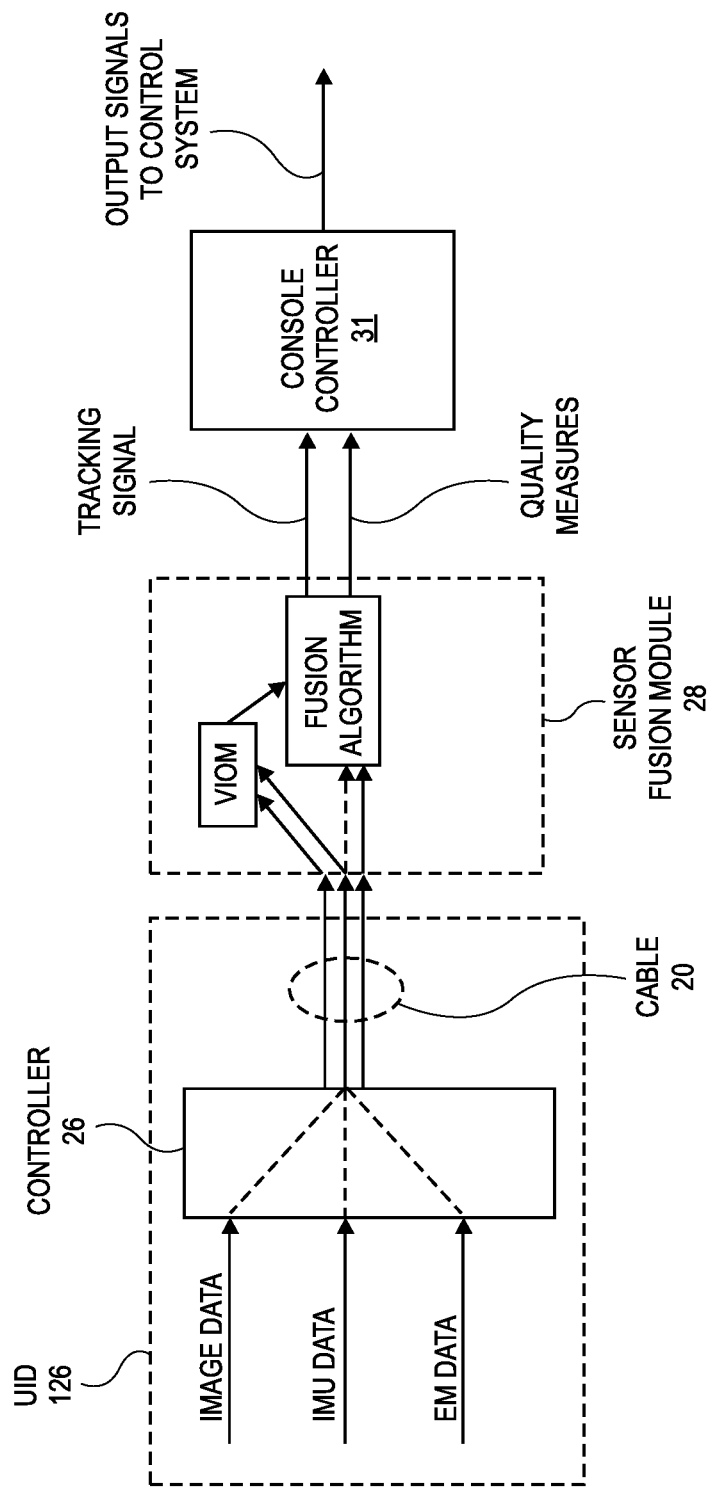
FIG. 8 is a block diagram of operations of a method of fusing spatial state signals that are representative of a pose of a user input device, to control motion of a surgical robotic system actuator, in accordance with an embodiment.

Still referring to FIG. 8, the grip data wire can carry the grip state data to the console controller 31 of the console computer. In an embodiment, the grip state data is stored and processed by a grip module 34 of the console controller 31. The console controller can include other modules to receive inputs from the user console components. For example, input data from seat controls can be stored and processed by a seat control module 35. The seat control inputs can be used to output actuator signals that cause the seat 122 to adjust for the operator 107. Similarly, input data from the foot pedals can be stored and processed by a pedal control 37. The pedal inputs can be used to output signals that cause various changes to the system, such as selecting elements in a graphical user interface, starting or stopping movement of the surgical tool, etc.

The console controller 31 can process the inputs received from the UID and the other components of the user console 120 to generate one or more output signals, which are transmitted to the surgical robotic system via a communication link. The output signals can be control signals to control movement of the arms and attached tools of the surgical robotic system. For example, at least one processor can be located in the control tower 130, and may be communicatively coupled to system components such as the surgical robotic platform 111 or one or more displays. Arm and/or tool actuators of surgical robotic system may receive control commands from this processor to cause motion corresponding to movement of the UID 126. More particularly, the control signals can cause the actuators to move the arms and/or tools of the surgical robotic system in coordination with changes in the UID pose.

Sensor Fusion

The UID having a camera and one or more tracking sensors as described above can generate several streams of tracking data that may be used to complement each other. For example, the IMU sensor and the EM sensor may be associated with inherent noise or drift that can result in tracking errors when using only IMU sensor data or only EM sensor data for tracking the pose of the UID. By contrast, the camera enables optical tracking of position and orientation, which is immune to the noise and drift that affects the other tracking sensors. Accordingly, optical tracking using the camera can work as a stabilizer to correct for errors in the data from the tracking sensors. More particularly, data from the camera and one or more of the EM sensor or the IMU sensor can be combined to generate the tracking signal that is fed to the tracking module 32 (FIG. 7) for use in controlling the surgical robotic system.

In an aspect, two or more of the visual information from the camera, the EM tracking information from the EM sensor, and the inertial measurement information from the IMU sensor are fused in the sensor fusion module 28 to enable stable and reliable estimation of the UID pose. The data from each UID sensor (e.g., camera, EM sensor, and IMU sensor) can be acquired and transmitted simultaneously by the UID to the sensor fusion module 28, which fuses information from the visual/inertial odometry module 30 and the EM tracking system 29. The visual/inertial odometry module 30 can fuse information from the camera and one or more IMU sensors. The sensor fusion module 28 can combine the data to correct error and noise of the data of one tracking modality with the data of another tracking modality. Accordingly, the estimation of UID pose can be more robust, e.g., less susceptible to the surrounding environment or noise, and can decrease jitter/noise that is inherent in any one of the tracking modality data streams. Furthermore, unlike conventional filtering of EM-based tracking signals that decrease noise in exchange for introduced latency (a measure of time between one event measured by a sensor and the next possible processing and assignment of a timestamp to the sensor measurement), a predictive model in the sensor fusion module 28, e.g., the EM tracking system 29 and/or the visual/inertial odometry module 30, can allow estimation of the tracking signal in real time.

Referring to FIG. 8, a block diagram of operations of a method of fusing spatial state signals from various sensors, to control motion of a surgical robotic arm actuator 114 is shown in accordance with an embodiment. The UID 126 can generate several spatial state signals, also referred to as input pose signals, in accordance with the pose of the UID, e.g., in response to movement of the device body 2. The camera of the UID 126 can generate image data that captures the markers that are in view of the camera in the UID. The IMU can generate IMU measurements that are streamed as IMU tracking data, corresponding to translational motion along several axes and rotational movement about the axes. Similarly, the EM sensor can generate EM measurements that are streamed as EM tracking data, corresponding to movement of the EM sensor within several degrees of freedom. These image data, IMU data, and EM data are shown in FIG. 8, indicating that the UID in this example includes each type of tracking sensor. However it will be appreciated that the UID need not have all of those sensors, and instead may only include two of those three sensor types. In any case, the data streams from different sensors are processed by the sensor fusion module 28 to generate a more robust and reliable tracking signal (that describes the UID pose) than can be achieved using only one of the sensor data streams alone.

In an embodiment, the data streams generated by each UID sensor are collected and aggregated by a processor of the UID controller 26. Aggregation of the data may include use of a buffer that simultaneously receives and outputs all data streams. For example, the image data can be sent into the buffer, and while the image data in the buffer is transmitted, additional tracking data from the IMU and/or EM sensor can be added to the transmission buffer. This process of simultaneous buffering of all tracking data can be contrasted with conventional techniques because ordinarily image data would be received, buffered, and sent sequentially with other data, rather than in parallel. Buffering all data streams in parallel, however, allows the large bandwidth and low latency transmission that is described above. More particularly, the continuous aggregation of image data interlaced with metadata describing UID pose can increase the transmission bandwidth and decrease the transmission latency as compared to a process that sequentially sends the image data as a complete packet followed by the IMU data followed by the EM data.

Each of the UID sensors may be comparatively better at detecting certain UID pose characteristics. For example, the EM sensor and the camera can provide more accurate position data than the IMU sensor. By contrast, the IMU sensor may provide better velocity information than the EM sensor or the camera. Similarly, each sensor may have unique drawbacks as compared to the other sensors. For example, the camera may be susceptible to occlusions by the operator or nearby objects that inadvertently block the image sensor's view of a marker. The EM sensor may be more susceptible to jitter than the other sensors. The IMU sensor may have more inherent drift than others. In an embodiment, the visual/inertial odometry module 30 as executed by a processor of the console computer 110 takes each of these relative pros and cons into account to effectively combine the individual sensor readings into a single output, e.g., a tracking signal, that accurately defines the UID pose.

The sensor fusion module 28 systematically fuses the multiple sensor data streams to enable de facto filtering of undesired frequency components, and robust and reliable estimation of the UID pose. In an embodiment, the sensor fusion module utilizes a linear quadratic estimator (LQE) for such filtering, that simultaneously corrects for noisy input data and up-samples the data rate to match a robot control algorithm update rate. This can be achieved by combining sensor streams in a Kalman filter, which is part of the LQE. Further specialization of the LQE concept can enable robust tracking using the input sensors. Based on a combination of the respective spatial state signals, e.g., the EM data and the IMU data, the sensor fusion module 28 can generate as its output not only the tracking signal corresponding to the pose of the UID but also a quality measure corresponding to a discrepancy between the respective spatial state signals. The output can be a low-latency signal at a higher update rate than each individual sensor source. Furthermore, the output signal may be smooth, which means that high-frequency components of the individual signals are removed by the estimation model of the sensor fusion module.

The sensor fusion module 28 can combine measurements of several sensors, e.g., the camera, the EM tracking system, and the IMU, to reliably determine the UID pose. The sensor fusion module 28 can include the visual-inertial odometry module 30 (VIOM 30), which receives the image data from the camera and the IMU data from the IMU. The visual/inertial odometry module can determine a pose of the UID based on the image data and the IMU data. The sensor fusion module can also include a sensor fusion algorithm, which can receive a processed tracking stream from the visual/inertial odometry module, which includes the combined camera and IMU data. The sensor fusion algorithm can also receive the EM data from the EM sensors. In an embodiment, the sensor fusion algorithm fuses the tracking streams of the camera view, the IMUD data, and the EM tracked pose. For example, the sensor fusion algorithm can combine the pose estimate output by the visual/inertial odometry module with an EM tracking pose estimate to generate the output tracking signal of the sensor fusion module 28.

It may be helpful to determine a spatial relationship between the sensors. In an embodiment, the data streams can be brought into the same coordinate system. This can be achieved based on a predetermined knowledge of the UID constructions. For example, a physical location of the IMU sensor within the device body 2 of the UID may be at a known distance along the central axis from the location of the EM sensor. This known distance can be used to reference the position and motion data derived from each sensor to a single, principal coordinate, such as a center of gravity of the UID that exists along the central axis between the IMU sensor and the EM sensor. The defined relationship between the sensors can be further refined by sampling sufficient corresponding output sequences from the sensors, and solving one or more equations (e.g., AX=XB, AY=YB, etc.) for the unknown spatial relationship.

In addition to relating the spatial positions of the sensors to each other, a temporal calibration of the sensors can be performed. Temporal calibration can detect when readings from the sensors arrive at the sensor fusion module 28, and can be a one-time calibration process that is performed at the beginning of each surgical operation. The temporal calibration can estimate a relative latency in the delivery of sensor data as between the different sensors, to establish a correlation between the measurements of the sensors, e.g., between measurements of the EM tracking system and the IMU tracking system.

Such accounting for the spatial and temporal relationships between measured sensor data enables the sensor fusion module 28 to use the received sensor data to estimate the UID pose in real time (with timely updates of the estimated UID pose, to ensure responsive and smooth control of the end effector on the robotic arm.) In an embodiment, one of the several UID sensors may update at a higher rate than another sensor. Based on the spatial and temporal correlations of the sensors, a difference in sensor readings can be continuously determined while monitoring the sensor that updates at the highest rate. The comparison can be used to continuously update position data of the UID and to detect divergence in sensor readings.

The sensor fusion module 28 can use the data from each tracking system to determine a bias of the tracking system. The bias includes characteristics of the tracking system, such as an expected noise profile, an expected accuracy, an expected drift, and other characteristics that define the system bias. These characteristics can be incorporated into a predictive model that may be part of a sensor fusion algorithm in the sensor fusion module 28 to estimate the UID pose based on fusing at least two tracking streams into a single tracking stream that is the estimate the UID pose.

Real-time sensor fusion may include generating a state vector for the UID, which is a prediction made by the model that combines a current position value of the UID with an expected position value of the UID. That is, in a prediction phase, a current UID pose can be estimated at high-frequency using previous sensor measurements and the predictive model. The latter incorporates forward-looking data derived from the previous sensor measurements, e.g., velocity data, to predict the current UID pose.

The state vector can be generated by the fusion algorithm, and can define the current pose of the UID. The state vector can include information about: a 6 degree of freedom pose measured by the EM tracking sensor (the EM sensor orientation and position relative to a global frame of reference), a linear velocity vector derived from IMU measurements, an angular velocity vector derived from IMU measurements, an acceleration derived from IMU measurements, a gravity direction derived from IMU measurements, a bias for the acceleration and angular velocity vectors based on determined biases of the IMU tracking system, and a predetermined 6 degree of freedom transformation from the IMU tracking system to the EM tracking system as determined by the spatial relationships of the sensors.

The state vector can be updated over time by minimizing accumulated error of constraints. More particularly, one or more of: a closeness or cycle constraint, an IMU constraint on acceleration, an IMU constraint on angular velocity, or a defined motion model constraint can have associated errors that are minimized to update the state vector. The IMU constraint on acceleration can constrain acceleration to be: $a = R\_world\_to\_IMU * G + b\_a$, where acc is an IMU measurement. The IMU constraint on angular velocity can constrain angular velocity to be: $w = omega + b\_w$, where w is an IMU measurement. The motion model constraint can define the motion model to be: $omega\_t = omega\_t-1$; $v\_t = v\_t-1 + (a - omega\_t-1 \text{ crossproduct } v\_t-1) * dt$; or $a = a\_t-1$.

In an embodiment, weights are assigned to each of the constraints. For example, the weights can correspond to the biases of the tracking systems that were previously identified. Alternatively, the weights can represent intrinsic error scores that can include information specific to a tracking system, such as the quality of the EM field. Such factors allow the system to determine how reliable the tracking system is at any point in time and weight the system readings accordingly.

The sensor fusion module 28 can rely on other mathematics to perform the estimation. The sensor fusion module can attempt to find a minimal accumulated error of the sum of the weighted constraints. The sensor fusion module can remove old states from the bundle using a Shur complement. The sensor fusion module can adjust the constraint weights to include orientation in the equations described above. Alternatively, orientation can be computed separately by use of the gyroscope measurements of the IMU in combination with the EMT orientation measurements. In addition, orientation averages can be computed using quaternions or rotation matrices. The sensor fusion module can model noise in order to improve fusion quality. Optionally, the sensor fusion module can run at a higher frequency to enable an increase of sampling rate.

Based on the model described above, the sensor fusion module 28 can output a tracking signal derived from the fused tracking stream, and the quality measure. The output tracking signal and quality measure can be transmitted to the console controller 31 for further analysis and use. More particularly, the console controller 31 can use the tracking signal and the quality measure to generate output signals for use by the digital control system software (e.g., that is being executed by one or more processors in the control tower 130) to control the associated surgical robotic arm 114 of the system.

The quality measure can correspond to a discrepancy between the EM measurements and the IMU measurements. For example, the quality measure can be a representation of a deviation of one of the sensor data streams. The quality measure can be based on covariances of the data streams. The quality measure may also represent an intrinsic error score for each of the individual tracking systems. The quality measure can be based on one or more of these factors, e.g., may be based on a combination of all of the factors.

In an embodiment, the quality measure can be used as an integrity check. The quality measure, which characterizes or compares the quality of sensor readings from the UID, can be compared to a predetermined threshold to determine whether the estimation of UID pose (given in the tracking signal from the sensor fusion module 28) is accurate. For example, the quality measure implies noise on each sensor, and when the noise exceeds a certain level, it can be determined that the pose estimation is unreliable (and that as a result motion of the associated end effector or tool on the associated robotic arm should be paused.) Accordingly, the console controller 31 may be configured to pause at least the associated end effector or tool (halt its motion) when the quality measure of its associated UID tracking is below a predetermined threshold, indicating excessive discrepancy between the readings from at least two of the tracking sensors.

The following additional statements of the disclosure are made, for a UID HAVING A CAMERA FOR VISUAL/INERTIAL ODOMETRY. 1. A user interface device (UID) for a surgical robotic system, comprising: a device body extending along a central axis; a plurality of grip linkages mounted on the device body around the central axis; and a camera mounted on the device body. 2. The UID of claim 1 further comprising one or more tracking sensors mounted within the device body, wherein the one or more tracking sensors are configured to generate a spatial state signal in response to movement of the device body. 3. The UID of claim 2, wherein the one or more tracking sensors includes an inertial measurement unit (IMU) and an electromagnetic (EM) sensor, and wherein the EM sensor is capable of measuring six degrees of freedom. 4. The UID of claim 1, wherein the camera is mounted on an end of the device body to view in a direction of the central axis away from the plurality of grip linkages. 5. The UID of claim 1 further comprising: a printed circuit board mounted within the device body, wherein the printed circuit board includes one or more processors coupled to an image sensor of the camera and coupled to an inertial measurement unit (IMU), wherein the image sensor generates visual data and the IMU generates inertial data; and a USB cable connected to the one or more processors to transmit the visual data and the inertial data. 6. The UID of claim 5, wherein the USB cable is a USB 3.0 version or higher.

The following additional statement of the disclosure can be made, for SENSOR FUSION. 1. A surgical robotic system, comprising: a user interface device (UID) having a device housing and a plurality of tracking sensors configured to generate respective spatial state signals in response to movement of the device housing; and a processor configured to generate, based on a combination of the respective spatial state signals, a tracking signal corresponding to a pose of the UID and a quality measure corresponding to a discrepancy between the respective spatial state signals. 2. The surgical robotic system of claim 1, wherein the plurality of tracking sensors include an electromagnetic (EM) sensor configured to generate EM measurements and an inertial measurement unit (IMU) configured to generate IMU measurements, and wherein the quality measure corresponds to a discrepancy between the EM measurements and the IMU measurements. 3. The surgical robotic system of claim 2, wherein the processor is configured to pause motion of a corresponding tool of the surgical robotic system when the quality measure is below a predetermined threshold.

In the foregoing specification, the invention has been described with reference to specific exemplary embodiments thereof. It will be evident that various modifications may be made thereto without departing from the broader spirit and scope of the invention as set forth in the following claims. For example, it was mentioned above that where the UID is ungrounded (unrestricted by mechanical linkages that constrain a size of the operators workspace) the operator could also perform teleoperation while away from the user console 120, e.g., at table side (beside the surgical robotic platform 111.) In such an embodiment, where the UID is tracked as described above using multiple tracking modalities that are operating simultaneously, there can be a marker 10 for the visual modality estimations that is located for example on the shoulders of the operator or on a ceiling above the location of the operator 107 (at table side.) The specification and drawings are, accordingly, to be regarded in an illustrative sense rather than a restrictive sense.

What is claimed is:

1. A user input device (UID) for a surgical robotic system, comprising:
a device body extending from a proximal end to a distal end, the device body configured to be held by an operator's hand for teleoperation of a surgical robotic arm with the distal end of the device body being forward of the proximal end, the proximal end is to be cupped in the operator's hand, and a plurality of grip linkages mounted on the device body around a central axis of the device body and configured to be manipulated by the operator's hand for teleoperation of an end effector coupled to the surgical robotic arm;
a camera having an image sensor and an imaging lens, the camera being mounted on the device body such that the imaging lens faces forward at the distal end of the device body to view a marker; and
a UID controller coupled to the image sensor, wherein the UID controller is to send digital images of the marker produced by the image sensor to a processor that computes a visual modality estimation of a pose of the UID based on detecting the marker in the digital images.

2. The UID of claim 1 further comprising a first tracking sensor mounted on the device body, wherein the first tracking sensor is configured to generate a first spatial state signal in response to movement of the device body and the UID controller is coupled to the first tracking sensor and configured to send the first spatial state signal from the first tracking sensor to the processor, and wherein the processor is to combine information from the visual modality estimation and the first spatial state signal to produce a tracking signal indicative of the pose of the UID.

3. The UID of claim 2 wherein the first tracking sensor is an electromagnetic, EM, tracking sensor.

4. The UID of claim 2 wherein the first tracking sensor is an inertial measurement unit, IMU, and the first spatial state signal comprises accelerometer measurements and gyroscope measurements.

5. The UID of claim 4 further comprising a second tracking sensor mounted on the device body and being an electromagnetic (EM) tracking sensor that is to generate a second spatial state signal in accordance with the pose of the UID and in six degrees of freedom, wherein the processor is to produce the tracking signal by combining information from the visual modality estimation, the first spatial state signal and the second spatial state signal.

6. The UID of claim 1 wherein the plurality of grip linkages are positioned behind the camera.

7. The UID of claim 2 further comprising
a serial data communications cable connected to the UID controller to transmit i) the digital images of the marker produced by the image sensor and ii) the first spatial state signal from the first tracking sensor, to the processor.

8. The UID of claim 7 further comprising a second tracking sensor mounted on the device body and being an electromagnetic (EM) tracking sensor that is to generate a second spatial state signal in accordance with the pose of the UID and in six degrees of freedom, wherein the processor is to produce the tracking signal by combining information from the visual modality estimation, the first spatial state signal and the second spatial state signal.

9. A user input device (UID) for a surgical robotic system, comprising:
a device body extending from a proximal end to a distal end, the device body configured to be held by an operator's hand for teleoperation of a surgical robotic arm with the distal end being forward of the proximal end and the proximal end is to be cupped in the operator's hand;
a camera having an image sensor and an imaging lens, the camera being mounted on the device body such that the imaging lens faces forward at the distal end of the device body to view a marker comprising a plurality of infrared light sources positioned on a user console of the surgical robotic system;

an electromagnetic, EM, tracking sensor mounted on the device body and that is to generate a first spatial state signal in accordance with the pose of the UID; and a UID controller coupled to the image sensor and the EM tracking sensor, wherein the UID controller is to send digital images of the marker produced by the image sensor and the first spatial state signal generated by the EM tracking sensor to a processor, wherein the processor is to compute a visual modality estimation of a pose of the UID, based on detecting the marker in the digital images, and combine the visual modality estimation with the first spatial signal to produce a tracking signal indicative of the pose of the UID.

10. The UID of claim 9 further comprising an inertial measurement unit, IMU, mounted on the device body, wherein the IMU is to produce a second spatial state signal in accordance with the pose of the UID, and the UID controller is coupled to the IMU and configured to send the first spatial state signal, the second spatial state signal, and the digital images of the marker to the processor, and wherein the processor is to produce the tracking signal by combining information from the visual modality estimation, the first spatial state signal, and the second spatial state signal.

11. The UID of claim 10 in combination with the processor computing a quality measure that is indicative of a discrepancy between i) EM tracking sensor measurements in the first spatial state signal and ii) IMU measurements in the second spatial state signal.

12. A method for teleoperation control of a surgical robotic arm in a surgical robotic system, the method comprising:

generating by a camera that is looking outward from a user input device, UID, of a surgical robotic system, a plurality of digital images that capture a marker comprising a plurality of infrared light sources positioned on a user console of the surgical robotic system;

digitally processing the digital images to detect an object in the digital images that corresponds to the marker;

interpreting the detected object to compute a visual modality estimation of a pose of the UID, wherein the visual modality estimation tracks movement of the UID; and generating actuator control commands to control the surgical robotic arm based on the visual modality estimation, to cause movement of an end effector coupled to the surgical robotic arm that mimics the movement of the UID.

13. The method of claim 12 further comprising generating by an electromagnetic, EM, tracking sensor a first spatial state signal in accordance with the pose of the UID; and combining information from the visual modality estimation and from the first spatial state signal to produce a tracking signal indicative of the pose of the UID, wherein generating the actuator control commands is based on the tracking signal.

14. The method of claim 12 further comprising:

generating by an inertial measurement unit, IMU, in the UID a first spatial state signal in accordance with the pose of the UID; and fusing, by the processor, information from the visual modality estimation and from the first spatial state signal, to produce a tracking signal indicative of the pose of the UID, wherein generating the actuator control commands is based on the tracking signal.

15. The method of claim 14 wherein the first spatial state signal comprises accelerometer measurements and gyroscope measurements.

16. The method of claim 14 further comprising:

generating by an electromagnetic (EM) tracking sensor in the UID a second spatial state signal in accordance with the pose of the UID and in six degrees of freedom;

fusing by the processor information from i) the visual modality estimation, ii) the first spatial state signal, and iii) the second spatial state signal, to produce the tracking signal.

17. The method of claim 16 further comprising computing a quality measure that is indicative of a discrepancy between i) EM tracking sensor measurements by the EM tracking sensor and ii) IMU measurements by the IMU, wherein generating the actuator control commands is based on the quality measure.

18. The method of claim 17 wherein the processor is configured to pause motion of the end effector coupled to the surgical robotic arm, despite continued movement of the UID, in response to the quality measure being below a predetermined threshold.

19. The method of claim 12 wherein the digital images are infrared images, and wherein digitally processing the digital images to detect the object that corresponds to the marker comprises accessing a stored data structure that describes the relative location of each of a plurality of objects that make up the marker.

20. The method of claim 19 wherein the plurality of infrared light sources are in an inverted-Y arrangement on a stand of an operator display of the user console, where the operator display is to display video from an endoscope during teleoperation.

* * * * *